United States Patent [19]
Gupta

[11] Patent Number: 6,106,286
[45] Date of Patent: Aug. 22, 2000

[54] METHOD AND DEVICE FOR ADMINISTERING MEDICINE TO THE PERIODONTIUM

[76] Inventor: Subhash Gupta, P.O. Box 1064, Leominster, Mass. 01453

[21] Appl. No.: 09/235,385

[22] Filed: Jan. 22, 1999

[51] Int. Cl.⁷ .................................................. A01N 18/00
[52] U.S. Cl. .......................... 433/80; 424/435; 424/444
[58] Field of Search ........................... 433/80, 215, 136; 424/49, 435, 444

[56] References Cited

U.S. PATENT DOCUMENTS

| | | | |
|---|---|---|---|
| 4,020,558 | 5/1977 | Cournut et al. | 433/80 |
| 4,175,326 | 11/1979 | Goodson | 433/80 |
| 4,321,038 | 3/1982 | Porteous | 433/136 |
| 4,522,593 | 6/1985 | Fischer | 433/136 |
| 4,654,373 | 3/1987 | Bertelli | 514/690 |
| 4,685,883 | 8/1987 | Jernberg | 433/80 |
| 4,764,377 | 8/1988 | Goodson | 433/80 |
| 4,892,482 | 1/1990 | Lococo | 433/136 |
| 5,358,403 | 10/1994 | Groth | 433/141 |
| 5,908,613 | 6/1999 | Bozzacco | 424/50 |
| 5,925,335 | 7/1999 | Shuch et al. | 424/49 |

*Primary Examiner*—Ralph A. Lewis
*Attorney, Agent, or Firm*—Nields, Lemack & Dingman; Brian M. Dingman

[57] ABSTRACT

A dental loop for delivering Coenzyme Q10 to the periodontium by direct physical contact therewith, and a method using such loop. The loop is a loop of plain gut defining a series of pockets for carrying a medicament. Coenzyme Q10 is placed within the pockets, so that it is available directly at the site to which said loop is applied. The loop is slipped over a tooth and placed against the periodontium, and left in place for sufficient time for the Q10 to dissolve and act, and the loop dissolve.

2 Claims, 1 Drawing Sheet

METHOD AND DEVICE FOR ADMINISTERING MEDICINE TO THE PERIODONTIUM

FIELD OF THE INVENTION

This invention relates to a method and device for administering medicine to the periodontium.

BACKGROUND OF THE INVENTION

Coenzyme Q10, disclosed in U.S. Pat. Nos. 5,908,613 and 5,925,335, is an orally absorbable gum tissue regenerating agent. It will be most useful if applied directly to the area to be treated, and left in contact with the area for about 40–45 minutes.

SUMMARY OF THE INVENTION

This invention features a dental loop for delivering Coenzyme Q10 to the periodontium by direct physical contact therewith, and a method using such loop. The loop is a loop of plain gut defining a series of pockets for carrying a medicament. Coenzyme Q10 is placed within the pockets, so that it is available directly at the site to which said loop is applied. The loop is slipped over a tooth and placed against the periodontium, and left in place for sufficient time for the Q10 to dissolve and act.

DESCRIPTION OF THE PREFERRED EMBODIMENTS

Figure 1:
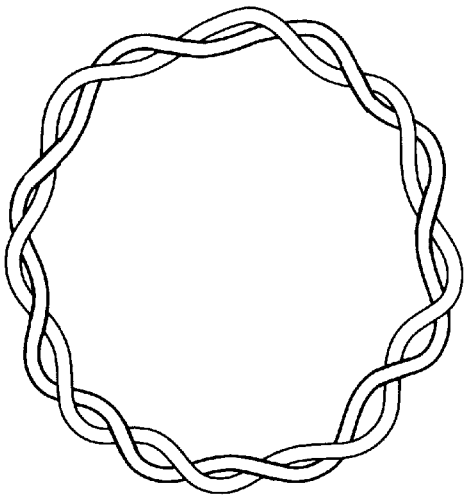
FIG. 1 is a top plan view of the dental loop of this invention.
Figure 2:
FIG. 2 is a side plan view thereof.
Figure 3:
FIG. 3 is a cross sectional view thereof.
Figure 4:
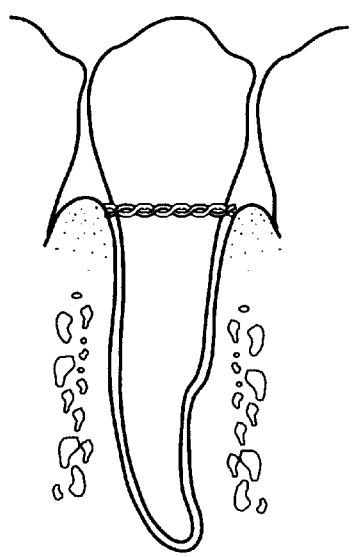
FIG. 4 is a view of the loop in position over a tooth and against the periodontium.

The loop is preferably of plain gut so that it dissolves in the mouth. The loop defines a series of pockets for carrying the Q10. When the loop is placed over a tooth and against the periodontium as shown in FIG. 4, the Q10 is delivered directly to the site at which is needed. The loop is left in place for at least about 40–45 minutes, so that the Q10 can act. Since the loop dissolves, it does not need to be removed.

The loop can be applied or stuck within the diseased gums to provide topical healing thereof. The topical application of coenzyme Q10 to the periodontal/gum pockets as a sole treatment reduces gingival crevicular fluid flow pocket depth and attachment loss, and application of coenzyme Q10 with subgingival mechanical debridement further improves modified gingival index, bleeding on probing, and peptidase activity of periodontopathic microorganisms.

The loop acts instantly within the diseased periodontium to produce locally its healing action and soothing effects. This action usually occurs within 4–5 minutes of its application and is present for the duration of the 40–45 minutes application period, and persists for 2–3 hours following.

What is claimed is:

1. A dental loop for delivering Coenzyme Q10 to the periodontium by direct physical contact therewith, comprising:

a loop of plain gut defining a series of pockets for carrying a medicament; and coenzyme Q10 within said pockets, so that it is available directly at the site to which said loop is applied.

2. A method of administering coenzyme Q10 directly to a diseased periodontium, comprising:

providing a loop of plain gut defining a series of pockets for carrying a medicament;

placing coenzyme Q10 within said pockets, so that it is available directly at the site to which said loop is applied;

placing said loop with Q10 over a tooth, and in contact with the periodontium; and maintaining the loop in place for at least about 40 minutes, to allow the Q10 to act on the periodontium around the loop location.

* * * * *